United States Patent
McDaniel

(10) Patent No.: US 9,089,339 B2
(45) Date of Patent: Jul. 28, 2015

(54) ELECTROPHYSIOLOGY CATHETER WITH IMPROVED TIP ELECTRODE

(75) Inventor: Benjamin David McDaniel, St. Vincent, CA (US)

(73) Assignee: Biosense Webster, Inc.

( * ) Notice: Subject to any disclaimer, the term of this patent is extended or adjusted under 35 U.S.C. 154(b) by 1598 days.

(21) Appl. No.: 11/696,257

(22) Filed: Apr. 4, 2007

(65) Prior Publication Data
US 2008/0249595 A1 Oct. 9, 2008

(51) Int. Cl.
*A61B 18/14* (2006.01)
*A61B 18/00* (2006.01)

(52) U.S. Cl.
CPC ... *A61B 18/1492* (2013.01); *A61B 2018/00148* (2013.01); *A61B 2018/00702* (2013.01); *A61B 2018/00791* (2013.01)

(58) Field of Classification Search
CPC ............... A61B 18/14; A61B 18/1492; A61B 2018/00071; A61B 2018/00077; A61B 2018/00083; A61B 2018/00089; A61B 2018/00107; A61B 2018/00148; A61B 2018/00577; A61B 2018/00702; A61B 2018/00791
USPC ............................ 606/41; 607/119, 122–128; 600/373–374
See application file for complete search history.

(56) References Cited

U.S. PATENT DOCUMENTS

| | | | |
|---|---|---|---|
| 4,532,924 A * | 8/1985 | Auth et al. | 606/50 |
| 5,281,218 A | 1/1994 | Imran | |
| 5,406,946 A * | 4/1995 | Imran | 600/374 |
| 5,423,807 A | 6/1995 | Milder | |
| 6,123,699 A | 9/2000 | Webster, Jr. | |
| 6,134,463 A * | 10/2000 | Wittkampf et al. | 600/374 |
| 6,171,277 B1 | 1/2001 | Ponzi | |
| 6,183,463 B1 | 2/2001 | Webster, Jr. | |
| 6,198,974 B1 | 3/2001 | Webster, Jr. | |
| 6,475,214 B1 | 11/2002 | Moaddeb | |
| 6,540,743 B2 * | 4/2003 | Olson et al. | 606/41 |
| 7,077,823 B2 | 7/2006 | McDaniel | |
| 2004/0054272 A1* | 3/2004 | Messing | 600/374 |
| 2004/0193152 A1 | 9/2004 | Sutton et al. | |
| 2005/0070887 A1* | 3/2005 | Taimisto et al. | 606/41 |
| 2005/0107783 A1 | 5/2005 | Tom | |
| 2005/0131508 A1* | 6/2005 | Garabedian et al. | 607/122 |
| 2005/0149009 A1 | 7/2005 | Wakikaido et al. | |
| 2005/0251125 A1* | 11/2005 | Pless et al. | 606/27 |
| 2006/0030844 A1* | 2/2006 | Knight et al. | 606/41 |
| 2008/0147046 A1 | 6/2008 | McDaniel | |

\* cited by examiner

*Primary Examiner* — Michael Peffley
*Assistant Examiner* — Samantha Good

(57) ABSTRACT

An EP catheter includes a tip electrode having a core primarily comprised of copper with an outer layer of a biocompatible metal disposed thereon exhibits appropriate electrical and thermal conduction characteristics while being cost-effective to produce. Alternatively, an inner layer of a biocompatible metal is disposed on the inside of the primarily copper core. Such a tip electrode may also be provided with irrigation lumens. Such a tip electrode could be manufactured from sheets of metal that upon extrusion would comprise the outer layer, core and optional inner layer respectively.

15 Claims, 5 Drawing Sheets

ELECTROPHYSIOLOGY CATHETER WITH IMPROVED TIP ELECTRODE

FIELD OF THE INVENTION

The present invention relates to a medical device for use in the vessel of a patient for the purpose of ablating tissue using radio frequency (RF) or other sources of energy. More particularly, the invention relates to an electrophysiology catheter having an improved tip electrode for ablation of tissue in a patient.

BACKGROUND OF THE INVENTION

Many abnormal medical conditions in humans and other mammals have been associated with disease and other aberrations along the lining or walls that define several different body spaces. In order to treat such abnormal conditions of the body spaces, medical device technologies adapted for delivering various therapies to the body spaces using the least invasive means possible.

As used herein, the term "body space," including derivatives thereof, is intended to mean any cavity within the body which is defined at least in part by a tissue wall. For example, the cardiac chambers, the uterus, the regions of the gastrointestinal tract, and the arterial or venous vessels are all considered illustrative examples of body spaces within the intended meaning.

The term "vessel," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of vessels within the intended meaning. Blood vessels are also herein considered vessels, including regions of the vascular tree between their branch points. More particularly, the pulmonary veins are vessels within the intended meaning, including the region of the pulmonary veins between the branched portions of their ostia along a left ventricle wall, although the wall tissue defining the ostia typically presents uniquely tapered lumenal shapes.

One means of treating body spaces in a minimally invasive manner is through the use of catheters to reach internal organs and vessels within a body space. Electrode or electrophysiology (EP) catheters have been in common use in medical practice for many years. They are used to stimulate and map electrical activity in the heart and to ablate sites of aberrant electrical activity. In use, the electrode catheter is inserted into a major vein or artery, e.g., the femoral artery, and then guided into the chamber of the heart that is of concern in order to perform an ablation procedure.

A typical ablation procedure involves the insertion of a catheter having a tip electrode at its distal end into a heart chamber. A reference electrode is provided, generally taped to the skin of the patient. RF (radio frequency) current is applied to the tip electrode, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue that is electrically non-conductive.

Tips of EP catheters for use in an ablation procedure typically are made from a platinum-iridium alloy. Although this material is not as thermally conductive as other materials such as copper or aluminum, the platinum-iridium alloy is more biocompatible than copper or aluminum. The platinum-iridium alloy, however, is costly to manufacture. Therefore, it would be desirable to provide an EP catheter having a tip electrode that is more thermally conductive than present EP tip electrodes but which would cost less to manufacture.

Additionally, it is difficult to solder leads to platinum-iridium tip electrodes for catheters. It would be preferable to have an EP tip electrode that would provide a platform for easier soldering of the leads.

Using pure gold would provide a tip electrode having high conductivity but would be prohibitively expensive. Therefore, it would be preferable to have an EP tip electrode that provides high-conductivity but at a lower cost than pure gold.

In RF ablation the tissue is heated sufficiently to cause cellular destruction in the cardiac tissue resulting in formation of a lesion within the cardiac tissue that is electrically non-conductive. During this process, heating of the electrode also occurs as a result of conduction from the heated tissue to the electrode itself. If the electrode temperature becomes sufficiently high, possibly above 60 degrees centigrade, a thin transparent coating of dehydrated blood protein can form on the surface of the electrode. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs and the catheter must be removed from the body and the tip electrode cleaned.

One method used to reduce the negative affects of heating is to irrigate the ablation electrode, e.g., with physiologic saline at room temperature, to actively cool the ablation electrode instead of relying on the more passive physiological cooling of the blood. Because the strength of the RF current is no longer limited by the interface temperature, current can be increased. This results in lesions that tend to be larger and more spherical, usually measuring about 10 to 12 mm. In addition to irrigation flow during ablation, a maintenance flow, typically at a lower flow rate, is required throughout the procedure to prevent backflow of blood flow into the coolant passages. Thus, it is necessary to provide for catheters that provide lumens for irrigation to the cool the tissue. Where irrigation is not possible it would be desirable to have an EP catheter that would act as a heat sink to cool tissue during ablation.

Another issue for EP catheters arises when they are used in RMT systems. In remote magnetic technology (RMT) systems, magnets external to the patient are used to produce magnetic fields in the patient that can guide a catheter such as an RF catheter for ablation. Catheters used for this purpose must have a high degree of flexibility so that the magnetic fields can properly guide the device through the tortuous anatomy of the patient. EP catheters used in RMT systems must also have reduced thermal reaction time and increased thermal accuracy. EP catheters for RMT systems are usually formed with a thin-walled shell that leaves room for a magnet used to navigate the tip of the catheter. This magnet causes the thermal conductivity of the tip of the RMT catheter to be much lower than it should ideally be. Therefore, it would be desirable to have an RMT catheter that increases the thermal conductivity of the shell material in order to compensate for the lack of thermal conductivity of the necessary magnets therein.

Additionally, as EP catheters become more complex, it would be desirable to have a tip electrode that would permit various sensors or other electronics to be housed while having similar thermal characteristics to existing EP catheter tips electrodes.

Also, in a feedback system in which tissue temperature changes are used to control the application of power to the ablation element it would be desirable to have an EP catheter tip electrode with a faster thermal reaction time in order to allow control with greater precision.

SUMMARY OF THE INVENTION

The present invention generally relates to an EP catheter having a tip electrode that is made from a plated base metal thereby providing an electrode that is biocompatible, highly thermally conductive and cost effective to manufacture. More specifically, the present invention provides a tip electrode having a core made of a base metal having high thermal and electrical conductivity such as copper or a copper alloy that is plated with a highly conductive metal having greater biocompatibility such as gold.

An EP catheter tip electrode in accordance with the present invention exhibits the biocompatibility of gold while being lower in cost to manufacture.

Furthermore, an EP catheter tip electrode in accordance with the present invention provides a highly thermally and electrically conductive tip electrode while being low in cost.

Additionally, the present invention improves manufacturability of EP catheters by providing a tip electrode that is easier to which it is easier to solder leads.

Still further, catheters in accordance with the present invention can provide an irrigated tip electrode with improved thermal characteristics or a tip electrode that behaves in a manner similar to an irrigated tip electrode by providing a heat sink for unwanted conductive heat.

Additionally, catheters in accordance with the present invention will provide an advantage of increased thermal conductivity to compensate for the low thermal conductivity of the magnets necessary for EP catheters when used in RMT systems.

Furthermore, in a feedback system in which tissue temperature changes are used to control the application of power to the ablation element an EP catheter tip electrode in accordance with the present invention will have a faster thermal reaction time providing temperature control with greater precision.

Specifically, the present invention is a catheter having an electrode that is comprised of at least a core and an outer layer disposed on the core. The core is preferably a highly conductive base metal such as copper but may also be made of copper, silver, gold, aluminum, beryllium, bronze or alloys thereof. A biocompatible outer layer is made of gold, platinum, or an alloy thereof. If the electrode is hollow there may also be an inner layer disposed within the core. Such an inner layer would be made of gold, platinum, silver or an alloy thereof. Additional layers may be used between the inner and outer layers.

One method of manufacturing the electrode of the present invention would be the extrusion of the electrode from stacked metal plates that would comprise the core, outer layer and inner layer. Other methods of manufacturing include stamping or deep drawing the hollow shell from the same.

DETAILED DESCRIPTION OF THE INVENTION

Figure 1:
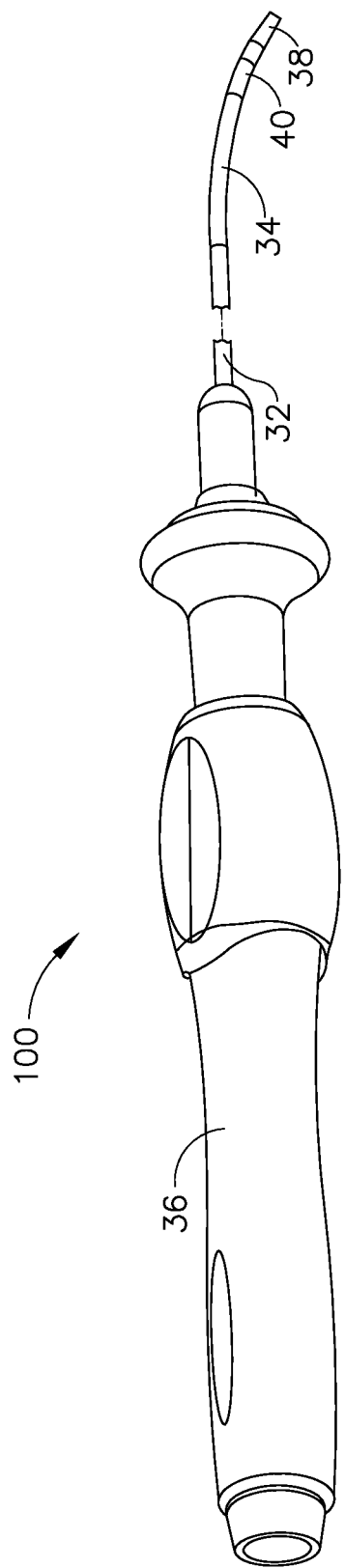
FIG. 1 is a perspective view of an EP catheter in accordance with the present invention.

FIG. 1 is a perspective view of an embodiment of a catheter in accordance with the present invention. As shown in FIG. 1, a preferred catheter 100 comprises an elongated tubular catheter body having a proximal section 32, a distal tip section 34 and a control handle 36 at the proximal end of the proximal section 32. Tip electrode 38 and optional ring electrode 40 are placed at or near distal tip section 34 so as to provide a source of ablation energy if the desired device is an RF ablation or EP mapping catheter.

Figure 2:
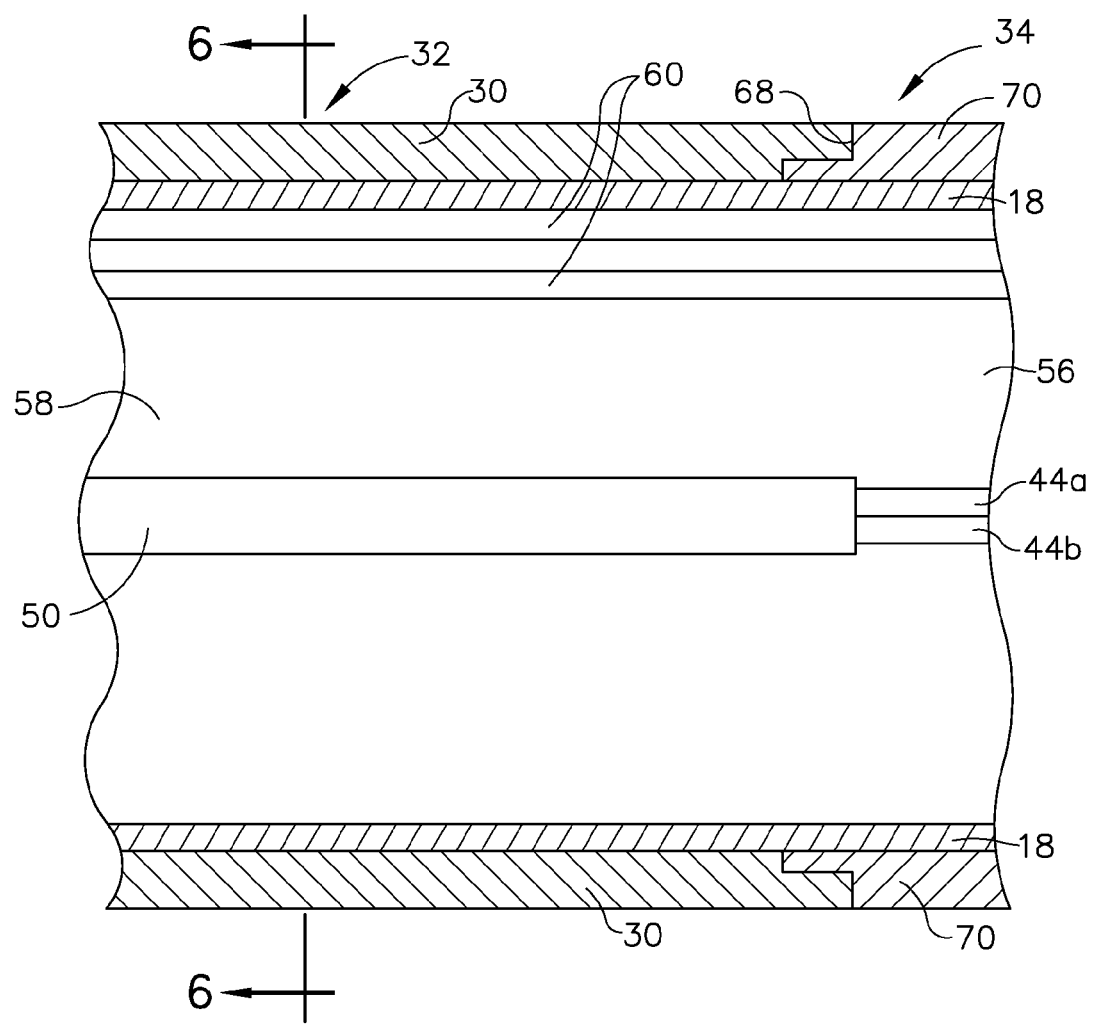
FIG. 2 is a longitudinal cross-sectional view of the flexible tubular section of the catheter of FIG. 1.
Figure 3:
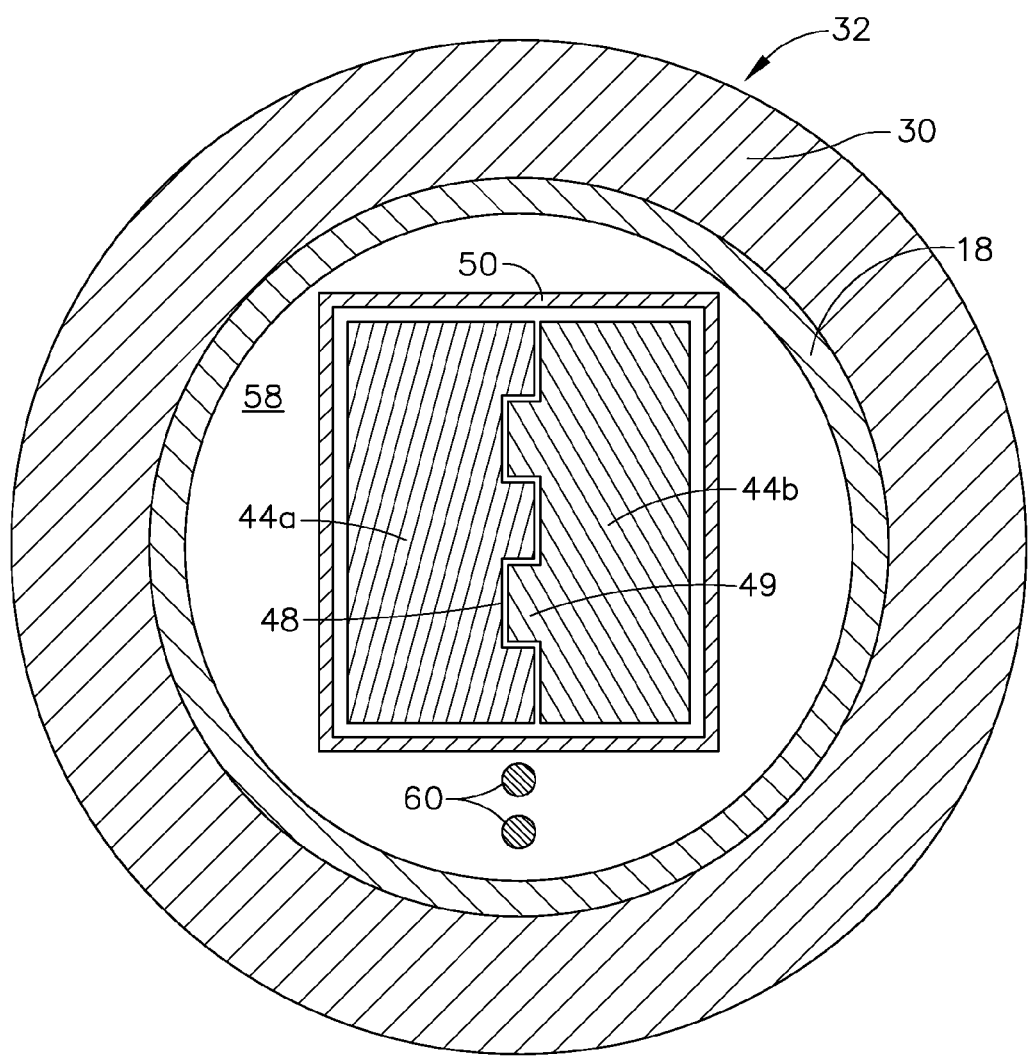
FIG. 3 is a cross-sectional view of the tubular section of the EP catheter of FIG. 2 through line 6-6.

As shown in FIGS. 2 and 3, section 32 comprises an elongated tubular construction having a single axial or central lumen 58. The proximal section 32 is flexible but substantially non-compressible along its length. Proximal section 32 can be made of any suitable construction and made of any suitable material. The preferred construction comprises an outer wall 30 made of polyethylene or PEBAX and an optional inner wall 18. The outer wall 30 may also comprise an imbedded braided mesh of stainless steel or similar material to increase torsional stiffness so that when control handle 36 is rotated the tip section 34 will rotate in a corresponding manner.

The overall length of the length of the catheter will vary according to its application for use but a preferred length is between approximately 90 and 120 cm and more preferably between approximately 100 and 110 cm. The outer diameter of the proximal section 32 is also a design characteristic that varies according to the application of the catheter but is preferably less than approximately 8 French (Fr). Optional inner wall 18 comprises a spirally-sliced tube (also referred to as a spirally-sliced tubular member) and is sized so that the outer diameter is about the same size or slightly smaller than the inner diameter of outer wall 30 thereby providing additional stiffness which can be controlled by the pitch angle of the cut as described above.

In the transition between the proximal section 32 and the distal section 34, outer wall 30 transitions to flexible tubing 70 having lumen 56 extending therethrough, although additional lumens can be included if desired such as for an irrigation lumen. Flexible tubing 70 is made of a suitable non-toxic material that is generally more flexible than the outer wall 30 of the proximal section 32. A presently preferred material for flexible tubing 70 is polyurethane although other materials such as nylon may also be used. The outer diameter of the distal section 34 is preferably no greater than about 8 Fr and is more preferable 6½ Fr or less. In the embodiment shown, the distal section 34 and the proximal section 32 are separate structures that have been fixedly attached to each other. It is understood that the distal section 34 and the proximal section 32 could be formed as a unitary structure as desired.

In the EP catheter of the present invention, tip electrode 38 and optional ring electrodes 40 are each electrically connected to a separate lead wires 60. Each lead wire 60 extends from the control handle 36 through the lumen 58 in the proximal section 32 and through lumen 56 in distal section 34 to tip electrode 38 and ring electrode 40. The proximal end of each lead wire 60 is connected to an appropriate connector (not shown) in the control handle 36 which can be plugged into a suitable source of RF energy.

In a bi-directional EP catheter a pair of puller wires 44a and 44b extend through the through the lumen 58 in the proximal section 32 and through lumen 56 in distal section 34. The puller wires are made of any suitable material such as stainless steel or Nitinol. Preferably, each puller wire 44 is covered with a lubricious coating such as PTFE or a similar material. Each puller wire 44 extends from the control handle 36 to near the tip of distal section 34. Puller wires 44 may be slidably mated to each other along a portion of their length in various manners such as that depicted in FIG. 6 in which puller wires 44a and 44b are interlocked. At their distal end the two puller wires 44a and 44b are fixedly attached to each other at a joint (not shown) by soldering, welding, bonding or similar method. Puller wires 44 can have any desired cross-sectional shape, e.g., round, rectangular, square, ellipsoidal, etc. and the cross-sectional shape of one wire does not need to be the same as the other. There are several ways in which the puller wires can be mated along their length including the generally rectangular notches 48 of puller wire 44a that mate with rectangular ribs 49 of puller wire 44b.

A sleeve 50 is provided that surrounds the puller wires to keep them in a closely adjacent relationship. Sleeve 50 may be made of any suitable material, e.g., polyamide or polyurethane or comprise a compression coil. Sleeve 50 may also be replaced with a spirally sliced tube as described in co-pending U.S. patent application Ser. No. 11/612,838 herein incorporated by reference.

Examples of other suitable control handles that can be used with the present invention are described in U.S. Pat. Nos. 6,123,699, 6,171,277, 6,183,463 and 6,198,974 the disclosures of which are hereby incorporated by reference. Additional configurations of puller wires 44 and gearing within the control handle may be used such as those disclosed in U.S. Pat. No. 7,077,823 which is also hereby incorporated by reference.

Figure 4:
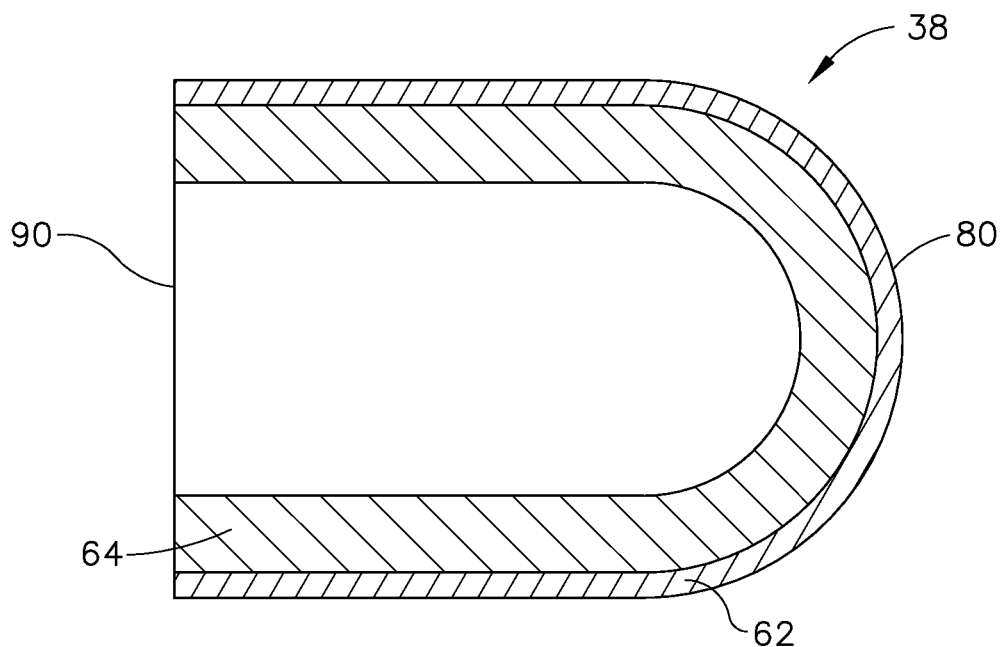
FIG. 4 is a cross-sectional view of an embodiment of an EP catheter tip electrode in accordance with the present invention.

FIG. 4 depicts a cross-section of an embodiment of an EP catheter tip in accordance with the present invention. Tip electrode 38 having a proximal end 90 and a distal end 80 is comprised of a core 64 with an outer layer 62 dispersed thereon. Core 64 can be made of copper, silver, gold, aluminum, beryllium, bronze or alloys thereof. Preferably, core 64 is made of a base metal having high conductivity but low cost. More preferably, pure copper or an alloy of copper and one or more other metals in which the copper content is significant, preferably more than approximately 90% by weight. Core 64 may be made in any known manner but the preferred method of manufacture is stamping, deep drawing or machining the core from a sheet of copper or copper alloy. Alternatively, core 64 may be extruded from the same type of sheet. Core 64 may be of any thickness that imparts structural integrity to the electrode while providing any necessary internal cavity for sensors and the like. Preferably, core 64 is between approximately 0.025 mm and 1.0 mm thick. Thickness may also vary across and around the core 64.

Outer layer 62 must be a metal having a high degree of biocompatibility such as gold, platinum, or an alloy thereof. Outer layer 62 is preferably gold or an alloy thereof. If outer layer 62 is a gold alloy it is preferable to have at least approximately 99% gold by weight in the alloy. Outer layer 62 is substantially thinner than the thickness of core 64. Outer layer 62 is preferably between approximately 0.05 mm and 1 mm in thickness. Outer layer 62 may be applied by known electroplating or other deposition processes such as vapor deposition—physical or chemical. Additionally, a stamping, drawing or extrusion process may also be used as described below.

Figure 5:
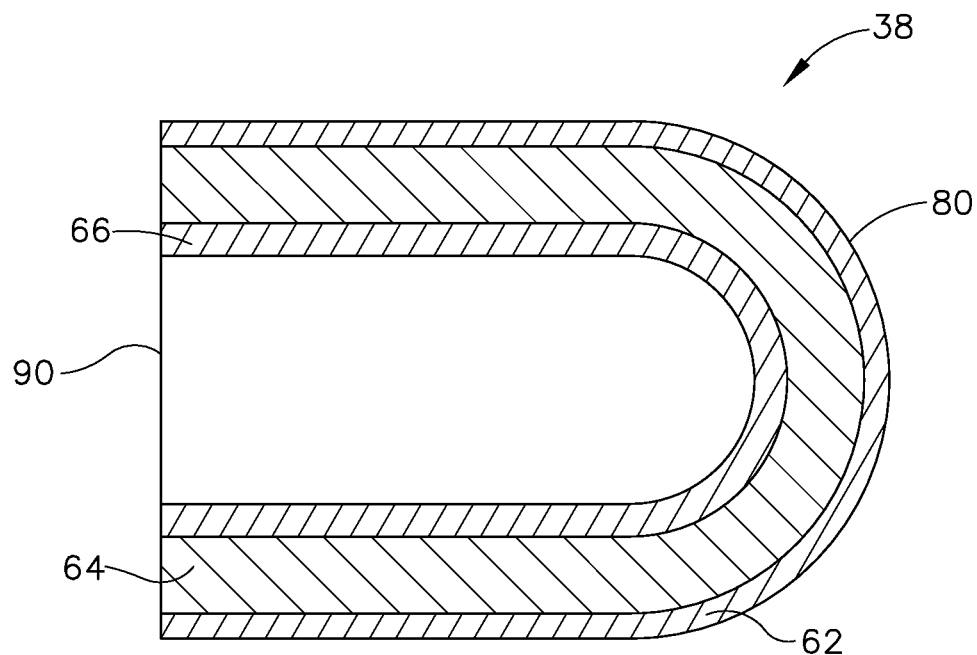
FIG. 5 is a cross-sectional view of a further embodiment of an EP catheter tip electrode in accordance with the present invention.

FIG. 5 depicts a cross-section of another embodiment of an EP catheter tip electrode 38 in accordance with the present invention. The tip electrode is similar to that described in FIG. 4 with the addition of an inner layer 66 dispersed on the inside surface of core 64. Inner layer 66 does not need to have a high degree of biocompatibility but it is easiest to use the same material for the inner layer 66 as for the outer layer 62 such as gold, platinum, or an alloy thereof. If a plating technique is used to manufacture the electrode, i.e., it would be difficult to plate the inside and outside of core 64 with different materials. Inner layer 66 is preferably gold or an alloy thereof. If the method of manufacture is not plating, but rather the extrusion, deep drawing or stamping of layered plates of materials then inner layer 66 could be a different alloy than outer layer 62. If inner layer 66 is a gold alloy it is preferable to have at least approximately 99% gold by weight in the alloy. Inner layer 66 is substantially thinner than the thickness of core 64. Inner layer 66 may be thinner than outer layer 62 but should be sufficiently thick to have enough integrity to perform its function within the intended constraints of the device without rubbing off, flaking or otherwise degrading. Inner layer 66 may be applied by known electroplating or other deposition processes such as vapor deposition—physical or chemical. It is also possible to use a gold wash for the inner layer rather than more expensive plating techniques.

Figure 6:
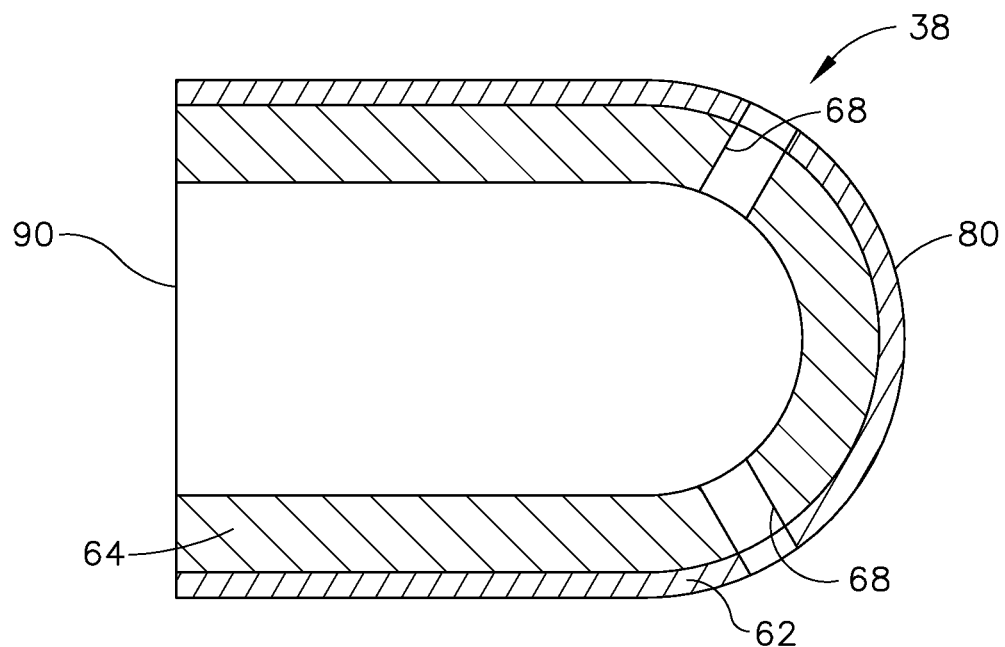
FIG. 6 is a cross-sectional view of an embodiment of an irrigated EP catheter tip electrode in accordance with the present invention.
Figure 7:
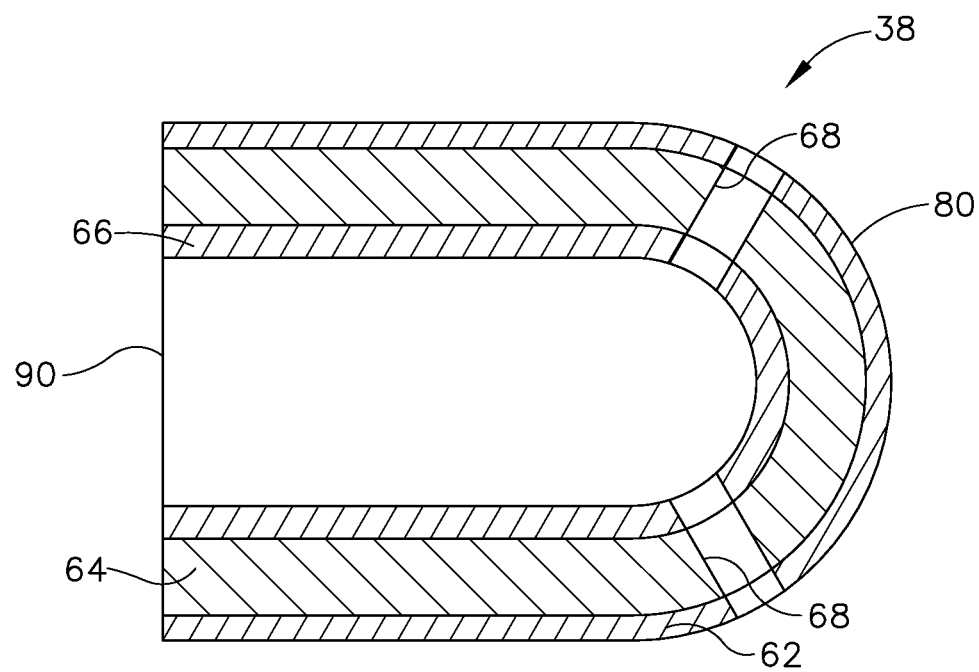
FIG. 7 is a cross-sectional view of a further embodiment of an irrigated EP catheter tip electrode in accordance with the present invention.

FIGS. 6 and 7 depicts cross-sections of the tip electrodes 38 of FIGS. 4 and 5 respectively with the addition of one or more irrigation lumens 68 for providing an irrigation fluid during ablation. Irrigation lumens 68 are connected to a fluid lumen (not shown) that transports the cooling or therapeutic fluid from outside the patient through EP catheter 100 to near the site of the ablation or other therapy.

The tip electrodes 38 depicted in FIGS. 4-7 may also be by stamping, drawing or extruding the desired shape for the electrode from two or three sheets of metal. In the case of the tip electrodes depicted in FIGS. 4 and 6 two sheets of metal or metal alloy with the thin outer layer disposed on the thicker core layer would be used. In the case of the tip electrodes depicted in FIGS. 5 and 7 three sheets of metal or metal alloy would be used with the core layer sandwiched between the outer layer and the inner layer. If the stamping, drawing or extruding process does not produce a layer of biocompatible material in any holes in the tip such as those depicted FIGS. 6 and 7 as irrigation lumens 68, an additional step of plating the holes with biocompatible material may be necessary.

Lead wires 60 are connected to the tip electrode 38 by soldering the lead wires to the predominantly copper core. Because lead wires are generally copper such soldering will be easier than soldering to a disparate metal.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter for use in a vessel comprising:
   an elongate tubular member having a proximal end and a distal end and having a lumen disposed therein;
   an electrode disposed near the tip of the distal end of the tubular member wherein the electrode is comprised of hollow core made entirely of an electrically conductive material having an outer surface and an inner surface with the hollow core having a thickness between approximately 0.025 mm and 1.0 mm to provide structural integrity to the electrode;
   an outer layer disposed on the entire outer surface of the hollow core and an inner layer disposed on the entire inner surface of the hollow core wherein both the inner layer and the outer layer are made of a same biocompatible material and wherein both the inner layer and the outer layer are substantially thinner than the hollow core; and,
   at least one lead wire extending from the proximal end of the elongate tubular member to the electrode.

2. The catheter of claim 1 wherein the core of the electrode is comprised of a base metal or alloy thereof also having high thermal conductivity.

3. The catheter of claim 2 wherein the electrically conductive material of the core of the electrode is comprised of copper or copper alloy.

4. The catheter of claim 3 wherein the biocompatible material is selected from the group consisting of: gold, platinum or an alloy thereof.

5. The catheter of claim 1 wherein the electrically conductive material of the core is comprised of a metal selected from the group consisting of: copper, silver, gold, aluminum, beryllium, bronze or alloys thereof.

6. The catheter of claim 5 wherein the biocompatible material selected from the group consisting of: gold, platinum or an alloy thereof.

7. The catheter of claim 1 wherein the elongate tubular member is a polymer.

8. The catheter of claim 7 wherein the polymer is selected from the group consisting of polyamide, polyurethane, nylon, PEBAX and PEEK polymers and blends thereof.

9. The catheter of claim 1 wherein the electrode is a tip electrode.

10. An electrode for an electrophysiology (EP) catheter comprising:
    a hollow core made entirely of an electrically conductive material having an inner surface and an outer surface and with the hollow core having a thickness between approximately 0.025 mm and 1.0 mm to provide structural integrity to the electrode;
    an outer layer disposed directly on the entire outer surface of the hollow core; and,
    an inner layer disposed directly on the entire inner surface of the hollow core; and
    wherein both the inner layer and the outer layer are made of a same biocompatible material and wherein both the inner layer and the outer layer are substantially thinner than the hollow core.

11. The electrode of claim 10 wherein the core is comprised of a base metal or an alloy thereof also having high thermal conductivity.

12. The electrode of claim 10 wherein the electrically conductive material of the core is comprised of copper or copper alloy.

13. The electrode of claim 12 wherein the biologically compatible metal is selected from the group consisting of: gold, platinum or an alloy thereof.

14. The electrode of claim 10 wherein the electrically conductive material of the core is comprised of a metal selected from the group consisting of: copper, silver, gold, aluminum, beryllium, bronze or alloys thereof.

15. The electrode of claim 14 wherein the biocompatible material is selected from the group consisting of: gold, platinum or an alloy thereof.

* * * * *